(12) United States Patent
Tomie et al.

(10) Patent No.: US 6,326,617 B1
(45) Date of Patent: Dec. 4, 2001

(54) PHOTOELECTRON SPECTROSCOPY APPARATUS

(75) Inventors: Toshihisa Tomie, Tsukuba; Hideaki Shimizu, Tsuchiura; Hiroyuki Kondo; Noriaki Kandaka, both of Tsukuba, all of (JP)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/145,064

(22) Filed: Sep. 1, 1998

Related U.S. Application Data
(60) Provisional application No. 60/057,892, filed on Sep. 4, 1997.

(51) Int. Cl.$^7$ ............................. C01N 23/00; G21K 7/00
(52) U.S. Cl. ............................................... 250/305
(58) Field of Search ................................... 250/305, 306, 250/281, 287, 309; 378/28, 119

(56) References Cited

U.S. PATENT DOCUMENTS
| | | | |
|---|---|---|---|
| 4,486,659 | * | 12/1984 | Turner ................................. 250/306 |
| 5,138,158 | * | 8/1992 | Ninomiya et al. ................... 250/305 |
| 5,569,916 | * | 10/1996 | Tomie ................................. 250/287 |

OTHER PUBLICATIONS
Kruit et al., "Magnetic Field Paralleliser for 2π Electron–Spectrometer and Electron–Image Magnifier," *J. Phys. E: Sci. Instrum.* 16:313–324 (1983).

Kondo et al., "Time–of–Flight Technique Photoelectron Spectroscopy with a Laser–Plasma X–Ray Source," *The Japan Society of Applied Physics and Related Societies*, p. 567, 29p–G–4. (In Japanese, with English abstract attached).

Kondo et al., "Time–of–Flight Technique Photoelectron Spectroscopy with a Laser–Plasma X–Ray Source (II)," *The Japan Society of Applied Physics and Related Societies*, p. 494, 26p–C–5. (In Japanese, with English abstract attached).

\* cited by examiner

*Primary Examiner*—Jack Berman
*Assistant Examiner*—Johnnie L Smith, II
(74) *Attorney, Agent, or Firm*—John P. White; Cooper & Dunham LLP (57) ABSTRACT

Photoelectron spectroscopy apparatus are disclosed that comprise a photoelectron detector and that exhibit improved performance of the photoelectron detector and thus more reliable and accurate analysis of photoelectron energy. In performing energy analysis of photoelectrons, the photoelectron detector measures the time distribution at which photoelectrons emitted from a specimen surface traverse a flight tube when the specimen is irradiated with X-rays from a pulse X-ray source. A magnetic field generator is situated near the specimen to collect and collimate photoelectrons emitted from the specimen surface and form a photoelectron flux inside a flight tube. Any one of a deflection electrode, electrostatic lens, magnetic field lens, or electromagnetic lens, or a combination thereof, is placed at the distal end of the flight tube in front of the photoelectron detector to disperse the photoelectron flux and increase the surface area in which the photoelectron flux is incident to the photoelectron-detection surface.

19 Claims, 2 Drawing Sheets

PHOTOELECTRON SPECTROSCOPY APPARATUS

This application claims benefit of Provisional Ser. No. 60/057,892 filed Sep. 4, 1997.

FIELD OF THE INVENTION

This invention pertains to photoelectron spectroscopy apparatus.

BACKGROUND OF THE INVENTION

Photoelectron spectroscopy (abbreviated "PES") is used to measure the energy distribution of electrons that are ejected by light quanta from atoms or molecules of a specimen. The specimen is bombarded with X-rays or vacuum ultraviolet light of a known energy hv. Absorption of the radiation causes emission of electrons (termed "photoelectrons") with varying kinetic energy. These kinetic energies are analyzed to obtain a photoelectron spectrum of the specimen. PES performed using vacuum ultraviolet light (a technique abbreviated "UPS") is mainly used to study valence electrons, and PES performed using X-rays (X-ray photoelectron spectroscopy, abbreviated "XPS") is used to study internal (i.e., core) electrons of the specimen.

In conventional XPS apparatus, X-rays are generated from an X-ray tube in which Al or Mg is used as a cathode material. However, because of the low brightness of X-ray tubes and the short wavelength of X-rays, the spatial resolution of conventional XPS is limited to around 10 $\mu$m. (Coxon et al., *J. Electron Spectrosc. Relat. Phenom.* 52:821 (1990). Recent trends in semiconductor manufacturing, materials science, and similar fields have greatly increased the demand for high spatial resolution XPS (abbreviated "$\mu$-XPS") systems.

Quite high spatial resolution can be achieved using fine X-ray optics to converge the X-ray from, for example, the undulator radiation of a synchrotron facility. However, a synchrotron facility is huge and ordinary surface analysts do not have ready access to such an XPS system. Furthermore, synchrotron-based XPS systems do not allow for the in-situ observations that are very important for evaluation of semiconductor devices and materials. Therefore, a practical laboratory-sized $\mu$-XPS system is strongly desired as an alternative to synchrotron-based XPS systems.

The concept of a laboratory-sized $\mu$-XPS system employing a laser-plasma X-ray source and Time-of-Flight (abbreviated "TOF") analysis of photoelectron energy was first proposed by Tomie (U.S. Pat. No. 5,569,916).

X-rays are generated by irradiating a target material with pulsed laser light that produces a plasma at the target. Such a laser-produced X-ray source is termed a "Laser-Plasma X-ray Source" (abbreviated "LPX" source). An LPX source is a compact and highly brilliant X-ray source and is thus suitable for use as an X-ray source for $\mu$-XPS.

In a TOF method of analysis, the energy of photoelectrons is determined from the time at which the photoelectrons arrive at the photoelectron detector and the distance from the specimen to the detector. Although the TOF method can be adopted only for a pulsed X-ray source, the efficiency with which such a method can detect photoelectrons can be many orders of magnitude greater than with other conventional methods.

Therefore, an XPS system employing LPX and TOF offers tantalizing prospects of providing a laboratory-sized $\mu$-XPS apparatus exhibiting short data-acquisition times. Inventors Kondo, Tomie, and Shimizu first demonstrated that such an XPS could provide photoelectron spectra even after only a few laser shots. *Advance Proceedings of the 42nd Conference of Applied Physics-Related Associations Lectures*, p. 567, Mar. 29, 1995.

In a TOF method, in order to increase the energy resolution of detected photoelectrons, an 10 electrical field is generated inside a "flight tube." The electrical field, which extends parallel to the flight tube, serves to decrease the velocity of the photoelectrons and correspondingly increase the time required for the photoelectrons to reach the photoelectron detector. Kondo, Tomie, and Shimizu, *Advance Proceedings of the 56th Applied Physics Society Conference Scientific Lectures*, p. 494, Aug. 26, 1995).

As the distance between the specimen and the photoelectron detector is increased, according to conventional wisdom, in order to increase the energy resolution of the photoelectrons, the solid angle at which the photoelectrons are collected and detected by the detector becomes correspondingly smaller. This causes a decrease in the number of detected photoelectrons, which lowers the signal-to-noise (S/N) ratio of the apparatus. Also, whereas the velocity component of the photoelectrons in the direction of the flight-tube axis is decreased due to photoelectron divergence, the component in a direction perpendicular to the axis is unchanged. The electrical field also bends the trajectories of the photoelectrons so that some of the photoelectrons (that would otherwise reach the photoelectron detector if the electrical field were not present) no longer reach the detector.

As the electrical field strength is increased to improve the energy resolution of the detected photoelectrons, fewer photoelectrons actually reach the detector. This deteriorates the S/N ratio even further. In order to compensate for the decrease in number of photoelectrons, photoelectrons are guided to the detector along magnetic field lines by placing the specimen inside a divergent magnetic field and by trapping and collimating the photoelectrons emitted from the specimen surface in the magnetic field lines. (The divergent magnetic field is termed a "magnetic bottle.") See, e.g., Kruit and Read, *J. Phys. E.* 16:313 (1983). The photoelectron flux can be expanded while being guided to the detector along the magnetic field lines, and the trajectory direction of the photoelectrons can be held nearly parallel to the axis of the flight tube. According to the thinking behind such apparatus, by applying such a "retarding field," there is no decrease in the number of detected photoelectrons since most of the photoelectrons are collimated in the flight tube. However, the magnification factor in the lateral direction resulting from application of such a divergent magnetic field is at most approximately 100×. E.g., if X-rays are converged onto a 1-$\mu$m locus on the specimen, the diameter of the photoelectron flux on the detector would be no more than approximately 100 $\mu$m. If a microchannel plate (MCP) were used as the photoelectron detector, photoelectrons would enter no more than a mere fifteen or so microchannels of the MCP.

On the other hand, if the number of photoelectrons entering such a small number of microchannels per unit time were to be increased, then a large current would flow through the affected microchannels. This would make the MCP susceptible to problems such as deteriorated response time, gain fluctuations, and damage, resulting in decreased MCP performance. Large numbers of electrons entering a microchannel on the detection surface per unit time in such a way causes substantial problems.

SUMMARY OF THE INVENTION

In view of the shortcomings of the photoelectron spectroscopy (PES) apparatus proposed by Tomie, as described above, an object of the present in invention is to provide PES apparatus that exhibit increased photoelectron-detector performance and, as a result, perform reliable and accurate photoelectron energy analysis.

To such end, and according to a first aspect of the invention, a photoelectron spectroscopy apparatus is provided that comprises an optical system, a flight tube, a photoelectron detector, a magnetic field generator, and an electron-controlling component.

The optical system is operable to converge a beam of vacuum ultraviolet or X-ray photons onto a locus of a specimen. The photons have sufficient energy to cause emission of photoelectrons from the locus of the specimen. The emitted electrons enter a proximal end of the flight tube.

The flight tube preferably comprises a coil extending lengthwise relative to the column; the coil is operable to produce a magnetic field to guide the photoelectrons as they propagate through the flight tube from the proximal end to a distal end of the flight tube. The flight tube also preferably comprises a magnetic shield to exclude terrestrial magnetism and/or to adjust the distribution of the magnetic field produced by the magnetic field generator.

The photoelectron detector (PED) is situated at the distal end of the flight tube and comprises a photoelectron-detecting surface. The PED is operable to measure a time distribution with which the photoelectrons propagate through the flight tube so as to allow an energy analysis of the photoelectrons to be made.

The magnetic field generator preferably comprises a magnet (e.g., electromagnetic, conventional magnet, or superconducting magnet) situated near a specimen and a coil extending lengthwise relative to the flight tube. The divergent magnet field produced by the magnetic field generator collects photoelectrons emitted from a surface of a specimen and collimates the photoelectrons to the axis of the flight tube.

The electron-controlling component preferably is selected from the group consisting of deflection electrodes, electrostatic lenses, magnetic field lenses, electromagnetic lenses, and combinations thereof. The electron-controlling component is situated between the distal end and the PED, and is operable to disperse the photoelectron flux and thus increase an area on the photoelectron-detection surface in which the photoelectron flux is incident.

For producing photoelectrons from core electrons of the specimen, the apparatus utilizes an X-ray beam to irradiate the specimen. Such apparatus can include a laser plasma X-ray source as defined herein. If X-rays are used, the optical system preferably comprises a Schwartzschild mirror.

The magnetic field generator preferably comprises an electromagnetic coil that surrounds the specimen. The electromagnetic coil is operable with the coil of the flight tube to produce a divergent magnetic field extending from the specimen into and through the flight tube. Thus, a lateral magnification factor of $(B_i/B_f)^{1/2}$ is preferably exhibited, wherein $B_i$ is the magnetic flux density on the specimen and $B_f$ is the magnetic flux density at the distal end of the flight tube.

The photoelectron-detection surface is preferably shaped such that the photoelectron pathlengths from the specimen to the photoelectron-detection surface are equal. Most preferably, the photoelectron-detection surface presents a concave surface toward the distal end of the flight tube.

The photoelectron spectroscopy apparatus also preferably comprises electrodes operable to generate a retarding field in the flight tube near the proximal end. The retarding field is sufficient to decrease the velocity of the photoelectrons propagating through the flight tube.

According to another aspect of the invention, methods are provided for performing photoelectron spectroscopy. In a first step of a preferred embodiment of such a method, a beam of vacuum ultraviolet or X-ray photons is directed toward a locus on a specimen. The beam has an energy level sufficient to cause emission of photoelectrons from the locus. In a second step, a magnetic field is generated substantially at the specimen that is sufficient to collect the photoelectrons emitted from the specimen into a photoelectron flux that enters and propagates through a flight tube extending from the specimen to a photoelectron detector. In a third step, a diverging magnetic field is generated that extends lengthwise along the flight tube to guide the photoelectron flux through the flight tube from a proximal end near the specimen to a distal end near the photoelectron detector. In a fourth step, as the photoelectrons exit the distal end of the flight tube; the photoelectron flux is caused to diverge so as to increase an area on the photoelectron-detection surface in which the photoelectron flux is incident.

The foregoing and additional features and advantages of the invention will be more readily apparent from the following detailed description which proceeds with reference to the accompanying drawings.

DETAILED DESCRIPTION OF PREFERRED EMBODIMENTS

General Features

In general, a PES apparatus according to the invention utilizes a beam of energetic photons such as vacuum ultraviolet light or X-rays that is directed so as to be incident on a locus on a specimen and cause the specimen to emit, from the locus, photoelectrons at discrete energy levels that can be analyzed. For use in analyzing valence electrons of the specimen, a vacuum ultraviolet light source can be used. X-rays, which are more energetic than ultraviolet light, are especially suitable for analyzing core electrons of the specimen.

In conventional UPS apparatus, vacuum ultraviolet light can be supplied by a He lamp. The harmonics generated from a pulse laser are more preferred for use in apparatus according to the present invention.

X-rays can be generated by a pulse X-ray source (e.g., a laser plasma X-ray source (LPX) or an X-ray laser). The X-rays are converged on a locus of the specimen by an X-ray optical element (e.g., a Schwartzschild mirror or Wolter mirror).

In any event, as a result of bombardment of the specimen by sufficiently energetic photons, photoelectrons are emitted from the specimen in various directions. According to the invention, almost all photoelectrons are trapped, expanded, and collimated by a magnetic field produced by a magnetic field generator situated in the vicinity of the specimen. The photoelectron flux propagates through a flight tube toward a photoelectron detector (PED).

As the emitted photoelectrons move from the specimen and into the flight tube, they exhibit a spiraling trajectory around the magnetic field lines of the divergent magnetic field. This spiraling trajectory continues as the photoelectrons pass through the flight tube to the PED. As a result, the photoelectrons reach the PED with high efficiency.

Analysis of the energy distribution of the photoelectrons is performed by measuring the distribution of "time of flight" (travel time) for the photoelectrons (which exhibit a corresponding distribution of kinetic energy) propagating from the specimen through the flight tube to the PED.

At the distal end of the flight tube and between the distal end and the PED is situated at least one of the following electron-controlling components: a deflector electrode, an electrostatic lens, a magnetic field lens, and an electromagnetic field lens. The component(s) serve to disperse the photoelectron flux and increase the area on the photoelectron-detection surface of the PED on which the photoelectron flux is incident.

The PED generates electrical signals exhibiting a characteristic that is a function of the kinetic energy of the photoelectrons incident on the PED and/or the binding energy of the photoelectrons. The electrical signals are conducted to a signal processor or the like that is operable to produce from such signals data sufficient to generate a photoelectron spectrogram for the specimen. Such a spectrogram is typically in the form of a plot of photoelectron binding energy (eV) versus intensity (number of photoelectrons) or a plot of photoelectron kinetic energy (eV) versus intensity. Such plots reveal peaks at discrete energy levels that provide information about the chemical composition and types of chemical bonds in the specimen.

Thus, the photoelectrons emitted from the specimen are picked up by the PED with high efficiency. The photoelectron flux is incident on a comparatively wide area of the photoelectron-detection surface of the PED without causing any decrease in PED performance. This allows reliable and accurate analysis of photoelectron energy.

When the photoelectron flux (exhibiting a distribution of kinetic energy) is dispersed as described above so as to increase the incident surface area of the flux on the PED, the individual pathlengths of photoelectrons having various kinetic energies respectively differ according to the degree of dispersion. E.g., a photoelectron having little kinetic energy is correspondingly greatly turned and its pathlength to the PED is lengthened. This can generate a shift in the time of flight corresponding to the increased pathlength relative to photoelectrons having greater kinetic energy. This can cause uncertainty in the individual photoelectron energies and a decrease in spectral resolution.

To prevent such a problem according to the invention, the photoelectron-detection surface of the PED preferably has a profile tending to equalize the pathlengths of the various photoelectrons traveling to the photoelectron-detection surface.

By way of example, the photoelectron-detection surface is preferably curved, as discussed in Example Embodiment 2, below.

It is also preferable to provide electrodes in the flight tube to generate a retarding field. The retarding field serves to lengthen the time of flight of the photoelectrons to the PED by decreasing the velocity of the photoelectrons through the flight tube. This serves to increase the energy resolution of the resulting photoelectronic spectrum.

This detailed description is augmented by the following description of two example embodiments. However, it will be understood that these example embodiments are not to be construed as limiting in any way.

EXAMPLE EMBODIMENT 1

Figure 1:
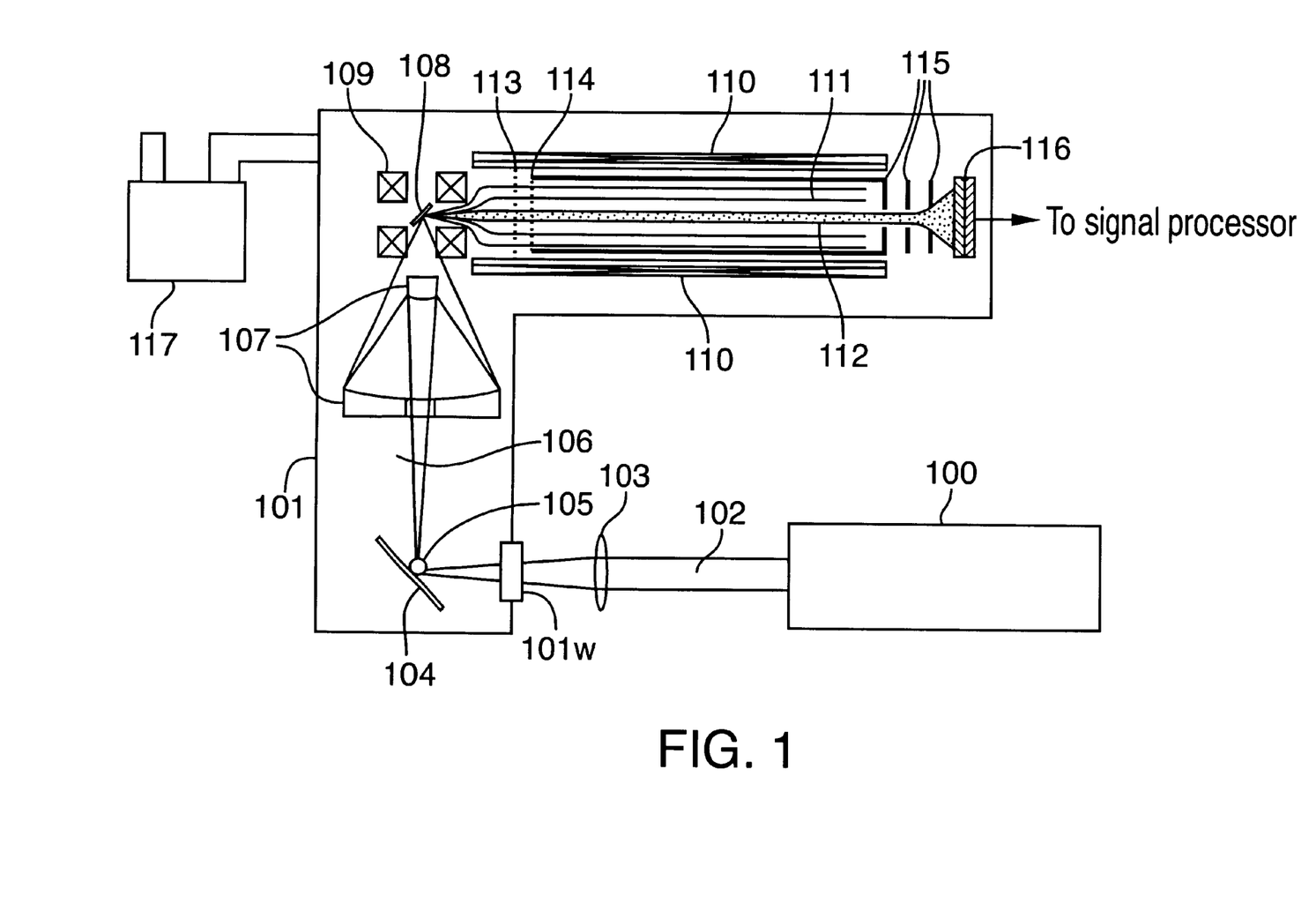
FIG. 1 is a schematic depiction of a photoelectron spectroscopy apparatus according to Example Embodiment 1.

A photoelectron spectroscopy apparatus according to this example embodiment is schematically depicted in FIG. 1, and is a representative example of an X-PES apparatus according to the invention. The apparatus comprises a vacuum chamber 101 situated to receive pulses of laser light 102 emitted from a pulse-laser source 100 and refracted by a lens 103. The vacuum chamber comprises a target 104, a filter 106 transmissive to X-rays but not to visible light, a Schwartzschild mirror 107, an electromagnet 109, a coil 110, electrodes 113, 114 for generating a retarding field, an electrostatic lens 115, a photoelectron detector 116 (preferably a microchannel plate (abbreviated "MCP")), and a vacuum pump 117.

In this example embodiment, pulsed laser light 102 from the pulse-laser source 100 passes through the lens 103 and enters the vacuum chamber 101 through a window 101W. The lens 103 converges the laser light 102 onto the target 104. Such irradiation of the target 104 converts the material of the target 104 into a plasma 105 that produces X-rays that propagate in pulses away from the plasma. Such an X-ray source is termed a "laser plasma X-ray source."

The interior of the vacuum chamber 101 is evacuated by the vacuum pump 117 to a vacuum level that is sufficiently permeable to X-rays.

The X-rays emitted from the plasma 105 pass through the filter 106 which is transmissive to X-rays but not to visible light. The X-rays are converged by the Schwartzschild mirror 107 (a representative X-ray optical element) onto a locus on a specimen 108.

The specimen 108 is situated within a strong magnetic field created by the electromagnet 109 that is positioned in close proximity to the specimen 108. The coil 110 produces a relatively weak but uniform magnetic field in the flight tube. The coil 110 extends away from the electromagnet 109 and defines a "flight tube" for photoelectrons emitted from the specimen when the specimen is bombarded at the locus by the X-rays. The flight tube is preferably appropriately shielded magnetically. The electromagnet 109, the coil 110, and the magnetic shield produce a magnetic field that preferably changes gradually from a strong field at a specimen position to a weaker field at a photoelectron detector 116.

As mentioned above, bombardment of a locus on the specimen 108 with the X-rays causes release of photoelectrons from the locus. The photoelectrons are emitted in various directions. Almost all photoelectrons emitted from the specimen can be trapped by the strong magnetic field and move to the photoelectron detector 116 with a helical motion along lines of magnetic field 111. These propagating photoelectrons are detected by the photoelectron detector 116 with excellent efficiency.

The respective velocity vectors of the photoelectrons in their spiraling trajectories extend in a direction roughly parallel to the axis of the flight tube. A photoelectron flux 112 passes down the flight tube along the velocity vectors to the photoelectron detector 116.

The lateral magnification factor of the photoelectrons after propagating down the flight tube in the divergent magnetic field is preferably $(B_i/B_f)^{1/2}$, wherein $B_i$ is the magnetic flux density on the specimen 108, and $B_f$ is the magnetic flux density at the distal end of the flight tube near the photoelectron detector 116. For example, if the magnetic flux density at the specimen 108 is 1T and the magnetic flux density at the distal end of the flight tube is $10^{-4} \cdot T$, then the lateral magnification factor is 100. Thus, if the X-rays are converged onto a 1-μm locus on the specimen 108, then a nearly parallel photoelectron flux having a diameter of 100 μm would be formed at the distal end of the flight tube.

The electrodes 113, 114 apply (generate) a retarding field. The electrodes 113, 114 are mounted inside the flight tube. The retarding field lengthens the time for the photoelectrons to reach the photoelectron detector 116 by decreasing the velocity of the photoelectrons. Such electrodes increase the energy resolution by which photoelectrons are detected by the photodetector 116.

The electrostatic lens 115 is preferably an aperture-type lens. The electrostatic lens 115 is used for diverging the photoelectron flux exiting the distal end of the flight tube so as to increase the surface area in which the photoelectron flux is incident on the surface of the photoelectron detector (e.g., MCP). The electrostatic lens 115 is mounted at or near the distal end of the flight tube and in front of the MCP 116. A voltage is applied to the electrostatic lens 115 so as to cause the photoelectron flux to become divergent.

The divergent photoelectrons downstream of the electrostatic lens 115 are detected by the photoelectron detector (e.g., MCP) 116.

The photoelectron spectroscopy apparatus of Example Embodiment 1 allows photoelectrons emitted from the specimen 108 to be detected with excellent efficiency. Thus, the FIG. 1 apparatus exhibits a data-acquisition time that is very short compared to conventional apparatus.

The magnetic field in the vicinity of the specimen is formed in Example Embodiment 1 by an electromagnet 109. However, a conventional magnet or superconducting magnet can be used to such end instead.

Further with respect to this example embodiment, an aperture-type electrostatic lens 115 is used to increase the area of the photoelectron-detection surface on which photoelectrons are incident. Alternatively, a cylindrical electrostatic lens or an electromagnetic lens can be used for such a purpose. The area of the photoelectron-detection surface can also be increased by using a deflection electrode or magnetic field lens, or a combination of one or more components from a group consisting of electrostatic lenses, electromagnetic lenses, deflection electrodes, and magnetic field lenses, instead of the electrostatic lens 115.

In addition, whereas an MCP is preferably used as a photoelectron detector in this example embodiment, an electron multiplier tube or channeltron could alternatively be used. This example embodiment is not specifically limited with respect to the type of detector so long as the detector is sensitive to photoelectrons.

EXAMPLE EMBODIMENT 2

Figure 2:
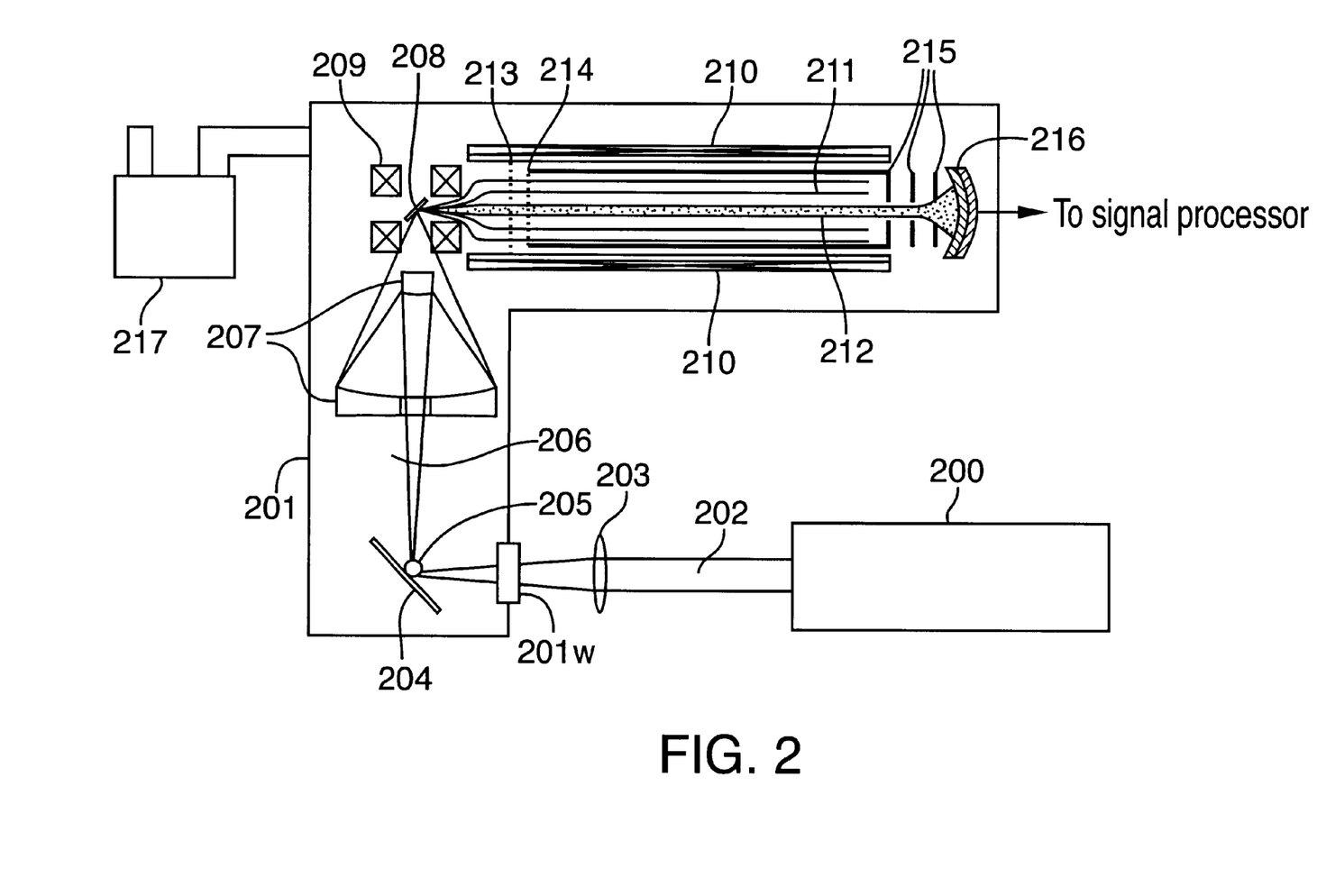
FIG. 2 is a schematic depiction of a photoelectron spectroscopy apparatus according to Example Embodiment 2.

A photoelectron spectroscopy apparatus according to this example embodiment is schematically depicted in FIG. 2.

The apparatus of Example Embodiment 2 is similar to Example Embodiment 1 except that the photoelectron-detection surface of the photoelectron detector is curved in Example Embodiment 2. Such curvature ensures that the energetic photoelectrons in the photoelectron flux that are incident on the photoelectron-detection surface have equal trajectory lengths from the specimen.

Many of the components of the FIG. 2 embodiment are similar to corresponding components in the FIG. 1 embodiment. Such components in the FIG. 2 embodiment include the pulsed laser source 200, the vacuum chamber 201 (with window 201W), the lens 203, the target 204, the filter 206 (transmissive to X-rays but opaque to visible light), the Schwartzschild mirror 207, the electromagnet 209, the coil 210, the electrodes 213 and 214, the electrostatic lens 215, the photoelectron detector (PED) 216, and the vacuum pump 217. These components are not described further.

As discussed above, the incident surface area of the photoelectron flux on the photoelectron-detection surface is increased by dispersing the photoelectron flux using a deflection electrode, magnetic field lens, or electron lens (electrostatic lens, electromagnetic lens), etc., as described above. The photoelectron flux comprises photoelectrons having various kinetic energy levels (i.e., the photoelectron flux exhibits a distribution of kinetic energy levels). Photoelectrons having such various kinetic energy levels will traverse correspondingly different pathlengths as they propagate through the electron-controlling component (e.g., deflection electrode, magnetic field lens, or the like). I.e., a photoelectron having a small kinetic energy level is more easily deflected in a magnetic or electric field. Thus, the distance traveled by such a photoelectron to reach the photoelectron-detection surface is longer than the distance traveled by a photoelectron having a greater kinetic energy. Consequently, the photoelectron having a lower kinetic energy takes more time to reach the photoelectron-detection surface than the photoelectron having higher kinetic energy.

Such differences in "time of flight" of photoelectrons emitted from otherwise similar molecular or atomic origins on the specimen surface can cause uncertainty in analysis of the photoelectron energy at the PED. This can cause a corresponding decrease in the energy resolution of the detected photoelectrons. In order to prevent such a problem, the photoelectron-detection surface of the PED 216 of the FIG. 2 embodiment is curved (concave) such that the pathlengths of the energetic photoelectrons in the photoelectron flux incident to the photoelectron-detection surface are equal. In other words, the photoelectron-detection surface of the PED 216 is curved to equalize the pathlengths of photoelectrons incident on the photoelectron-detection surface regardless of the kinetic energy levels of the photoelectrons in the photoelectron flux.

Thus, the photoelectron spectroscopy apparatus of Example Embodiment 2, in addition to exhibiting the advantages described in Example Embodiment 1, minimizes uncertainty in photoelectron kinetic energy levels and improves the energy resolution of detected photoelectrons.

In Example Embodiment 2, whereas an MCP is preferably used as the PED 216, an electron multiplier tube or channeltron, for example, can alternatively be used. This example embodiment is not specifically limited as to the type of photoelectron detector that is used.

The divergent magnetic field in the vicinity of the specimen 208 is preferably formed in Example Embodiment 2 by the electromagnet 209. Alternatively, for example, a conventional magnet or superconducting magnet can be used.

In Example Embodiment 2, an aperture-type electrostatic lens 215 is preferably used to increase the surface area on which photoelectrons are incident on the photoelectron-detection surface. Alternatively, a cylindrical electrostatic lens or an electromagnetic lens can be used. The surface area on which photoelectrons are incident on the photoelectron-detection surface can also be increased by using a deflection electrode or magnetic field lens, or a combination of at least one component selected from a group consisting of electrostatic lenses, electromagnetic lenses, deflection electrodes, and magnetic field lenses, rather than an electrostatic lens or electromagnetic lens alone.

In addition, a laser-plasma X-ray source as described above is preferably used as the pulse X-ray source in Example Embodiment 2. Alternatively, the X-ray source can be an X-ray laser or high-frequency pulsed laser light, for example.

Although a Schwartzschild mirror 207 is preferably used as the X-ray converging optical component, a total-reflection mirror such as an ellipsoidal multilayer or Wolter mirror, for example, or a zone plate can alternatively be used.

Apparatus according to the invention allow photoelectrons emitted from the specimen to be picked up with excellent efficiency. The photoelectron flux from the specimen enters a wide area on the photoelectron-detection surface of a downstream photoelectron detector. Consequently there is no decrease in performance which was caused by entering a high photoelectron flux density on PED, as described above. Also, reliable and accurate photoelectron energy analysis can be performed using apparatus according to the present invention, without experiencing uncertainty in the measured photoelectron energy and without experiencing deteriorations in the energy resolution of the detected photoelectrons.

With a photoelectron spectroscopy apparatus of this invention, the time required for the photoelectrons to reach the photoelectron detector can be lengthened by decreasing the velocity of the photoelectrons, thereby increasing the energy resolution.

Whereas the invention has been described in connection with several example embodiments representing the current best mode of the invention, it will be understood that the invention is not limited to those example embodiments. On the contrary, the invention is intended to encompass all alternatives, modifications, and equivalents as may be included within the spirit and scope of the invention, as defined by the appended claims.

What is claimed is:

1. A photoelectron spectroscopy apparatus, comprising:
   (a) an optical system for converging a beam of vacuum ultraviolet or X-ray photons onto a locus of a specimen, the photons having an energy level sufficient to cause emission of photoelectrons from the locus;
   (b) a flight tube comprising a proximal end situated adjacent the specimen, a distal end, and a longitudinal axis;
   (c) a photoelectron detector situated adjacent the distal end of the flight tube and comprising a photoelectron-detection surface, the photoelectron detector being operable to measure a time distribution with which photoelectrons propagate through the flight tube from the proximal end to the distal end so as to allow an energy analysis of the photoelectrons to be made;
   (d) a magnetic field generator comprising (i) a magnet situated near the specimen, and (ii) a coil extending lengthwise relative to the flight tube, the magnetic field generator producing a divergent magnetic field that collects photoelectrons emitted from the locus and collimates the collected photoelectrons to the axis of the flight tube as the photoelectrons propagate from the proximal end to the distal end;
   (e) the flight tube comprising a magnetic shield for performing at least one of (i) excluding terrestrial magnetism from inside the flight tube and (ii) adjusting a magnetic field distribution in the flight tube produced by the magnetic field generator; and
   (f) at least one electron-controlling component that includes at least one deflection electrode, electrostatic lens, magnetic field lens, or electromagnetic lens, the electron-controlling component being situated between the distal end of the flight tube and the photoelectron detector and being operable to disperse the photoelectron flux and increase an area on the photoelectron-detection surface in which the photoelectron flux is incident.

2. The photoelectron spectroscopy apparatus of claim 1, exhibiting a lateral magnification factor, from the proximal end to the distal end of the flight tube, of $(B_i/B_f)^{1/2}$, wherein $B_i$ is the magnetic flux density on the specimen and $B_f$ is the magnetic flux density at the distal end of the flight tube.

3. The photoelectron spectroscopy apparatus of claim 1, wherein the magnet is an electromagnet.

4. The photoelectron spectroscopy apparatus of claim 1, wherein the electron-controlling component is operable independently from the magnetic field generator to disperse the photoelectron flux collimated by the divergent magnetic field.

5. The photoelectron spectroscopy apparatus of claim 1, wherein the magnet is a conventional magnetic.

6. The photoelectron spectroscopy apparatus of claim 1, further comprising a laser plasma X-ray source.

7. The photoelectron spectroscopy apparatus of claim 6, wherein the optical system comprises a Schwartzschild mirror.

8. The photoelectron spectroscopy apparatus of claim 1, wherein the magnetic field generator comprises an electromagnetic coil surrounding the specimen, the electromagnetic coil being operable with the coil of the flight tube to produce a diverging magnetic field extending from the specimen into the proximal end of the flight tube.

9. The photoelectron spectroscopy apparatus of claim 8, exhibiting a lateral magnification factor, from the proximal end to the distal end of the flight tube, of $(B_i/B_f)^{1/2}$, wherein $B_i$ is the magnetic flux density on the specimen and $B_f$ is the magnetic flux density at the distal end of the flight tube.

10. The photoelectron spectroscopy apparatus of claim 1, wherein the photoelectron-detection surface is shaped such that photoelectron pathlengths from the proximal end to the photoelectron-detection surface are equal.

11. The photoelectron spectroscopy apparatus of claim 10, wherein the photoelectron-detection surface presents a concave surface toward the distal end of the flight tube.

12. The photoelectron spectroscopy apparatus of claim 1, further comprising an electrode operable to apply a retarding field in the flight tube near the proximal end, the retarding field being sufficient to decrease the velocity of the photoelectrons propagating through the flight tube.

13. A photoelectron spectroscopy apparatus, comprising:
   (a) a source of a beam of vacuum ultraviolet or X-ray photons having an energy level sufficient to cause emission of photoelectrons from a locus of a specimen;
   (b) an optical system for converging the beam of photons onto the locus of a specimen;
   (c) a flight tube through which the photoelectrons emitted from the specimen propagate, the flight tube comprising a proximal end situated adjacent the specimen, a distal end, and a coil extending lengthwise relative to the flight tube, the coil being operable to guide the photoelectrons as the photoelectrons propagate through the flight tube from the proximal end to the distal end;
   (d) a photoelectron detector situated at the distal end of the flight tube, the photoelectron detector comprising a photoelectron-detection surface and being operable to measure a time distribution with which the photoelectrons propagate through the flight tube so as to allow an energy analysis of the photoelectrons to be made, the photoelectron-detection surface being shaped such that photoelectron pathlengths from the specimen to the photoelectron-detection surface are substantially equal;

(e) an electromagnetic coil surrounding the specimen near the proximal end of the flight tube, the electromagnetic coil being operable to collect the photoelectrons emitted from the specimen to form a photoelectron flux that enters and propagates through the flight tube, and being operable with the coil of the flight tube to produce a diverging magnetic field extending from the specimen into the proximal end of the flight tube;

(f) at least one electron-controlling component that includes at least one deflection electrode, electrostatic lens, magnetic field lens, or electromagnetic lens, the electron-controlling component being situated between the distal end of the flight tube and the photoelectron detector and being operable to disperse the photoelectron flux and increase an area on the photoelectron-detection surface in which the photoelectron flux is incident; and (g) an electrode operable to apply a retarding field in the flight tube near the proximal end, the retarding field being sufficient to decrease the velocity of the photoelectrons propagating through the flight tube.

14. A method for performing photoelectron spectroscopy, comprising the steps:

(a) directing toward a locus on a specimen a beam of ultraviolet or X-ray photons having an energy level sufficient to cause emission of photoelectrons from the locus on the specimen;

(b) generating a field at the specimen sufficient to collect the photoelectrons emitted from the locus into a photoelectron flux that enters and propagates through a flight tube extending from the specimen to a photoelectron detector;

(c) generating a magnetic field extending lengthwise along the flight tube to guide the photoelectron flux through the flight tube from a proximal end adjacent the specimen to a distal end adjacent the photoelectron detector; and (d) as the photoelectrons exit the distal end of the flight tube, causing the photoelectron flux to diverge so as to increase an area on the photoelectron-detection surface in which the photoelectron flux is incident.

15. A photoelectron spectroscopy apparatus, comprising:

(a) an optical system for converging a beam of vacuum ultraviolet or X-ray photons onto a locus of a specimen, the photons having an energy level sufficient to cause emission of photoelectrons from the locus;

(b) a flight tube comprising a proximal end situated adjacent the specimen, a distal end, and a longitudinal axis;

(c) a photoelectron detector situated adjacent the distal end of the flight tube and comprising a photoelectron-detection surface, the photoelectron detector being operable to measure a time distribution with which photoelectrons propagate through the flight tube from the proximal end to the distal end so as to allow an energy analysis of the photoelectrons to be made;

(d) a magnetic field generator comprising (i) a magnet situated near the specimen, (ii) a coil extending lengthwise relative to the flight tube, and (iii) an electromagnetic coil surrounding the specimen, the magnetic field generator producing a divergent magnetic field that collects photoelectrons emitted from the locus and collimates the collected photoelectrons to the axis of the flight tube as the photoelectrons propagate from the proximal end to the distal end, and the electromagnetic coil being operable with the coil of the flight tube to produce a diverging magnetic field extending from the specimen into the proximal end of the flight tube;

(e) the flight tube comprising a magnetic shield for performing at least one of (i) excluding terrestrial magnetism from inside the flight tube and (ii) adjusting a magnetic field distribution in the flight tube produced by the magnetic field generator; and (f) at least one electron-controlling component that includes at least one deflection electrode, electrostatic lens, magnetic field lens, or electromagnetic lens, the electron-controlling component being situated between the distal end of the flight tube and the photoelectron detector and being operable to disperse the photoelectron flux and increase an area on the photoelectron-detection surface in which the photoelectron flux is incident, wherein the photoelectron spectroscopy apparatus exhibits a lateral magnification factor, from the proximal end to the distal end of the flight tube, of $(B_i/B_f)^{1/2}$, wherein $B_i$ is the magnetic flux density on the specimen and $B_f$ is the magnetic flux density at the distal end of the flight tube.

16. A photoelectron spectroscopy apparatus, comprising:

a flight tube comprising a proximal end and a distal end, the proximal end situated adjacent a specimen;

a photoelectron detector situated adjacent the distal end of the flight tube; and at least one electron-controlling component situated between the distal end of the flight tube and the photoelectron detector, the electron-controlling component including at least one deflection electrode, electrostatic lens, magnetic field lens, or electromagnetic lens and being operable to disperse a photoelectron flux received from the flight tube.

17. A photoelectron spectroscopy apparatus, comprising:

(a) an optical system for converging a beam of vacuum ultraviolet or X-ray photons onto a locus of a specimen, the photons having an energy level sufficient to cause emission of photoelectrons from the locus;

(b) a flight tube comprising a proximal end situated adjacent the specimen, a distal end, and a longitudinal axis;

(c) a photoelectron detector situated adjacent the distal end of the flight tube and comprising a photoelectron-detection surface, the photoelectron detector being operable to measure a time distribution with which photoelectrons propagate through the flight tube from the proximal end to the distal end so as to allow an energy analysis of the photoelectrons to be made;

(d) a magnetic field generator comprising (i) a magnet situated near the specimen, and (ii) a coil extending lengthwise relative to the flight tube, the magnetic field generator producing a divergent magnetic field that collects photoelectrons emitted from the locus and collimates the collected photoelectrons to the axis of the flight tube as the photoelectrons propagate from the proximal end to the distal end such that a lateral magnification factor, from the proximal end to the distal end of the flight tube, of $(B_i/B_f)^{1/2}$ is produced, wherein $B_i$ is the magnetic flux density on the specimen and $B_f$ is the magnetic flux density at the distal end of the flight tube;

(e) the flight tube comprising a magnetic shield for performing at least one of (i) excluding terrestrial magnetism from inside the flight tube and (ii) adjusting a magnetic field distribution in the flight tube produced by the magnetic field generator; and (f) at least one electron-controlling component that includes at least one deflection electrode, electrostatic lens, magnetic field lens, or electromagnetic lens, the electron-controlling component being situated between the distal end of the flight tube and the photoelectron detector and being operable to disperse the photoelectron flux and increase an area on the photoelectron-detection surface in which the photoelectron flux is incident.

18. The photoelectron spectroscopy apparatus of claim 17, wherein the magnetic field generator comprises an electromagnetic coil surrounding the specimen, the electromagnetic coil being operable with the coil of the flight tube to produce a diverging magnetic field extending from the specimen into the proximal end of the flight tube.

19. A photoelectron spectroscopy apparatus, comprising:

a flight tube comprising a proximal end and a distal end, the proximal end situated adjacent a specimen;

a photoelectron detector situated adjacent the distal end of the flight tube; and at least one electron-dispersing component situated between the distal end of the flight tube and the photoelectron detector, the electron-dispersing component including at least one deflection electrode, electrostatic lens, magnetic field lens, or electromagnetic lens and being operable to disperse a photoelectron flux received from the flight tube.

* * * * *

UNITED STATES PATENT AND TRADEMARK OFFICE
CERTIFICATE OF CORRECTION

PATENT NO.      : 6,326,617 B1                                                Page 1 of 1
DATED           : December 4, 2001
INVENTOR(S)     : Tomie et al.

It is certified that error appears in the above-identified patent and that said Letters Patent is hereby corrected as shown below:

Column 2,
Line 7, "an 10 electrical" should read -- an electrical --

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,326,617 B1
DATED : December 4, 2001
INVENTOR(S) : Tomie et al.

It is certified that error appears in the above-identified patent and that said Letters Patent is hereby corrected as shown below:

<u>Title page,</u>
Item [73], Assignee, "Synaptic Pharmaceutical Corporation, Paramus, NJ (US)" should read -- The National Institute of Advanced Industrial Science and Technology and Nikon Corporation, Tokyo, Japan --
Item [74], *Attorney, Agent, or Firm*, "John P. White; Cooper & Dunham LLP" should read -- Klarquist Sparkman, LLP --

Signed and Sealed this

Twenty-seventh Day of January, 2004

JON W. DUDAS
*Acting Director of the United States Patent and Trademark Office*